United States Patent [19]
Schmidt

[11] Patent Number: 6,110,157
[45] Date of Patent: Aug. 29, 2000

[54] DISPOSABLE ABSORBENT ARTICLE HAVING AN INTEGRATED FASTENING SYSTEM

[75] Inventor: Sheila Abel Schmidt, Appleton, Wis.

[73] Assignee: Kimberly-Clark Worldwide, Inc., Neenah, Wis.

[21] Appl. No.: 08/393,970

[22] Filed: Feb. 24, 1995

[51] Int. Cl.$^7$ ................................................. A61F 13/16
[52] U.S. Cl. ...................................... 604/385.1; 604/392
[58] Field of Search ........................... 604/385.1, 387, 604/389, 390, 391, 392, 393; 2/49.1, 112, 94

[56] References Cited

U.S. PATENT DOCUMENTS

| | | | |
|---|---|---|---|
| D. 343,681 | 1/1994 | Hull | D24/126 |
| 1,649,958 | 11/1927 | Hoyme | 604/392 |
| 2,273,542 | 2/1942 | Tasker | 128/284 |
| 3,110,312 | 11/1963 | Wirth . | |
| 3,386,442 | 6/1968 | Sabee | 604/385.1 |
| 3,890,973 | 6/1975 | Davis et al. . | |
| 4,560,380 | 12/1985 | Tharel | 604/385 |
| 4,585,447 | 4/1986 | Karami | 604/385 |
| 4,728,326 | 3/1988 | Gilles | 604/391 |
| 4,769,023 | 9/1988 | Goebel et al. | 604/385 |
| 4,771,483 | 9/1988 | Hooreman et al. | 604/392 |
| 4,798,603 | 1/1989 | Meyer et al. | 604/378 |
| 4,838,886 | 6/1989 | Kent | 604/392 |
| 4,909,802 | 3/1990 | Ahr et al. | 604/392 |
| 4,909,808 | 3/1990 | Ahr et al. | 604/385.1 |
| 4,961,737 | 10/1990 | Orlando | 604/385.2 |
| 4,995,873 | 2/1991 | Knight | 604/391 |
| 5,135,522 | 8/1992 | Fahrenkrug et al. | 604/385.1 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,204,997 | 4/1993 | Suzuki et al. | 2/400 |
| 5,209,743 | 5/1993 | Hardison | 604/391 |
| 5,374,262 | 12/1994 | Keuhn, Jr. et al. | 604/391 |

FOREIGN PATENT DOCUMENTS

| | | |
|---|---|---|
| 0167931 | 1/1986 | European Pat. Off. . |
| 0235815 | 9/1987 | European Pat. Off. . |
| WO84/04242 | 11/1984 | WIPO . |
| WO9426222 | 11/1994 | WIPO . |
| WO9426224 | 11/1994 | WIPO . |
| WO9426225 | 11/1994 | WIPO . |

*Primary Examiner*—Glenn K. Dawson
*Assistant Examiner*—David J. Cho
*Attorney, Agent, or Firm*—Jeffrey B. Curtin

[57] ABSTRACT

The present invention concerns a disposable absorbent article which has an integrated fastening system. The disposable absorbent article comprises an outer cover, a bodyside liner, an absorbent core disposed between the bodyside liner and the outer cover and an integrated fastening system. The integrated fastening system comprises a pair of belt segments which are provided by and at least partially detachable from the longitudinal end portions or side portions of the absorbent article. Each of the belt segments includes a free end which is configured to be detachable from the absorbent article. The integrated fastening system also comprises a fastening means for attaching the free end of each of the belt segments to the absorbent article to maintain the absorbent article about a waist of a wearer when in use. A reinforcement panel may also be located on the portion of the absorbent article used to provide the belt segments to reinforce the belt segments.

34 Claims, 5 Drawing Sheets

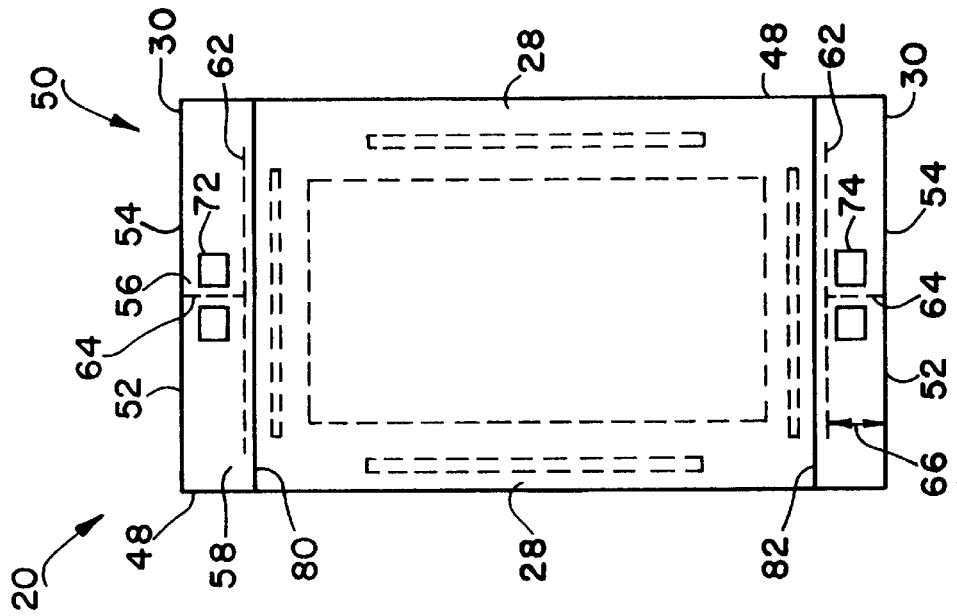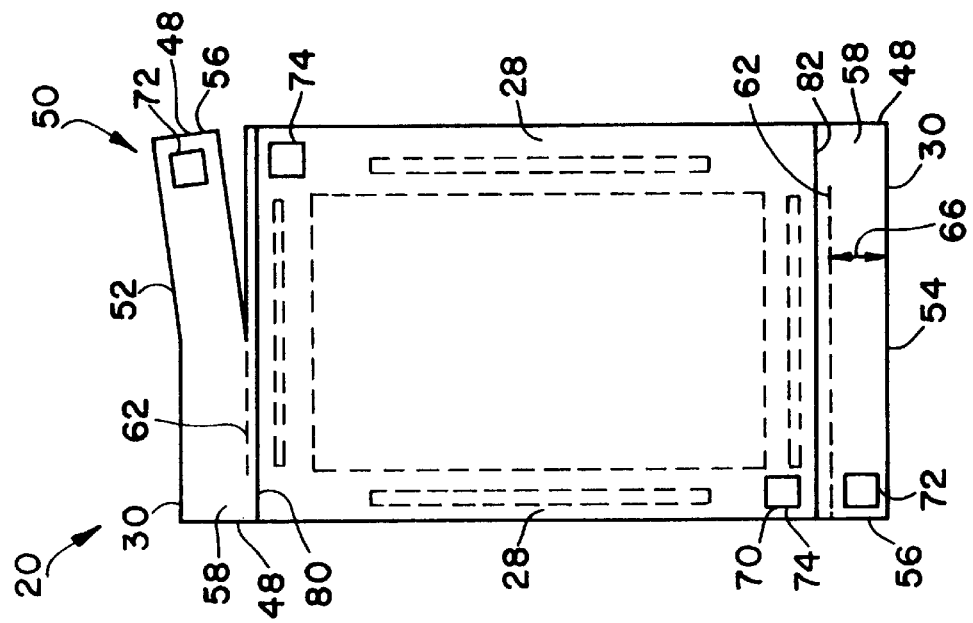

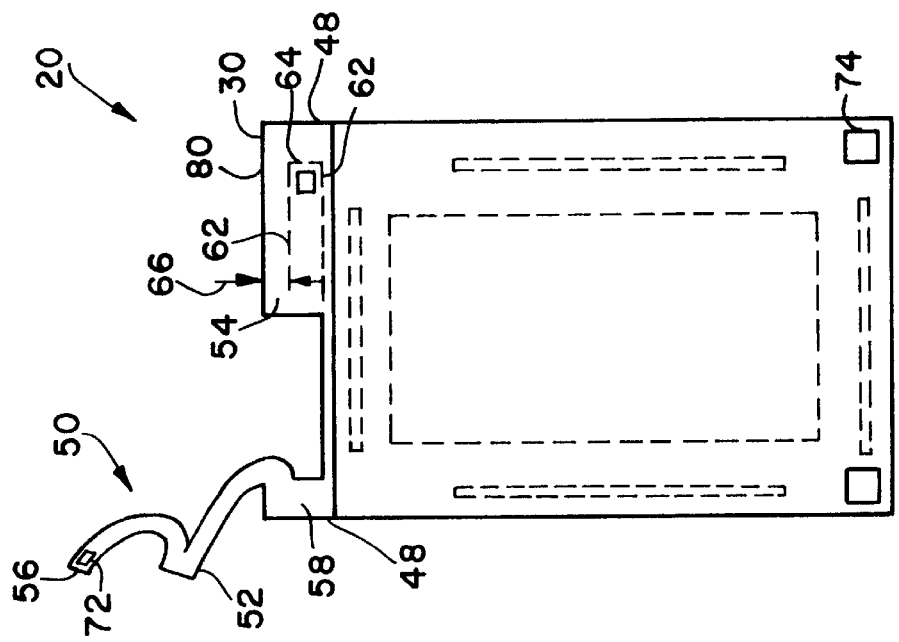
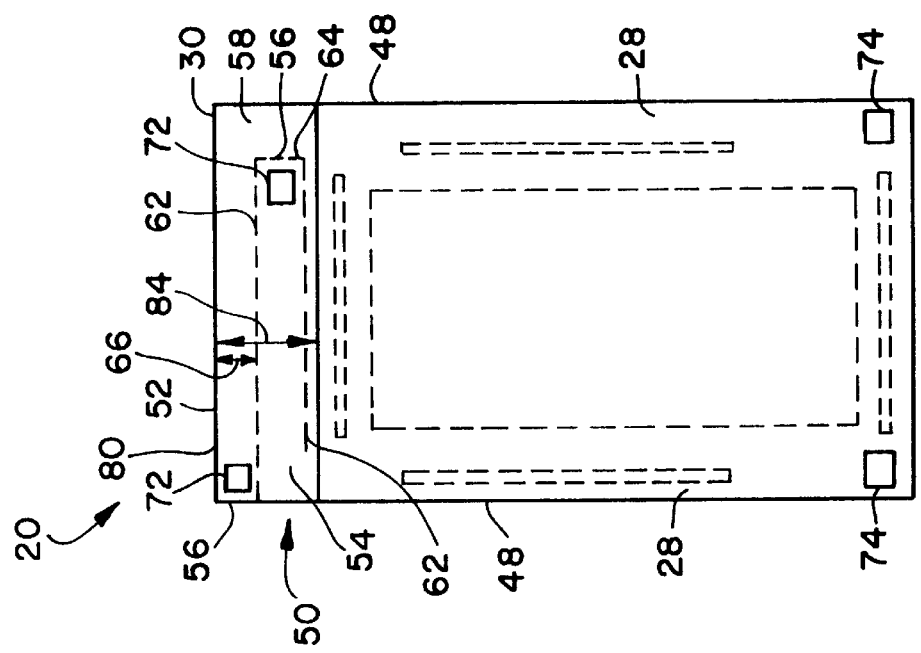

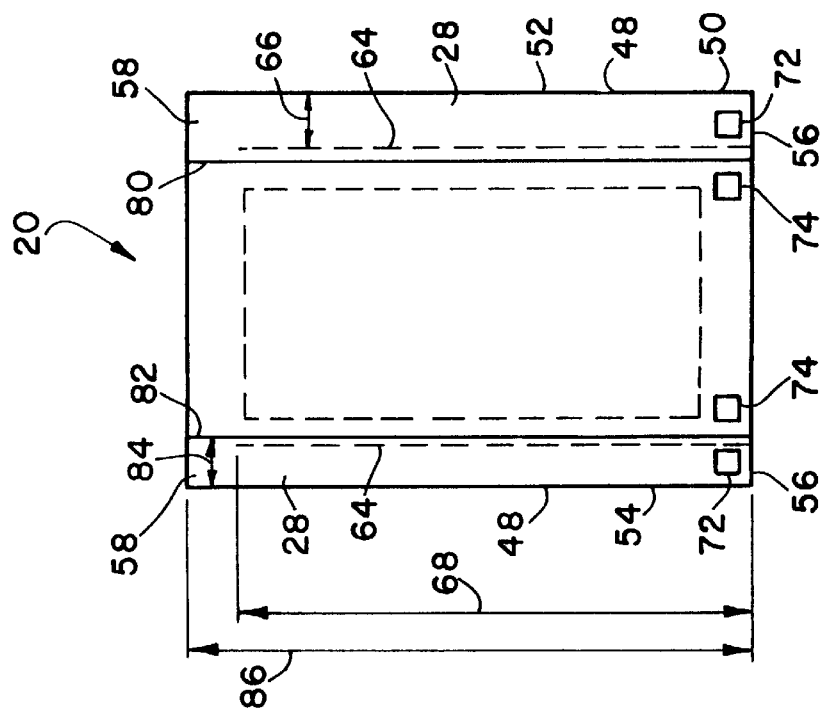
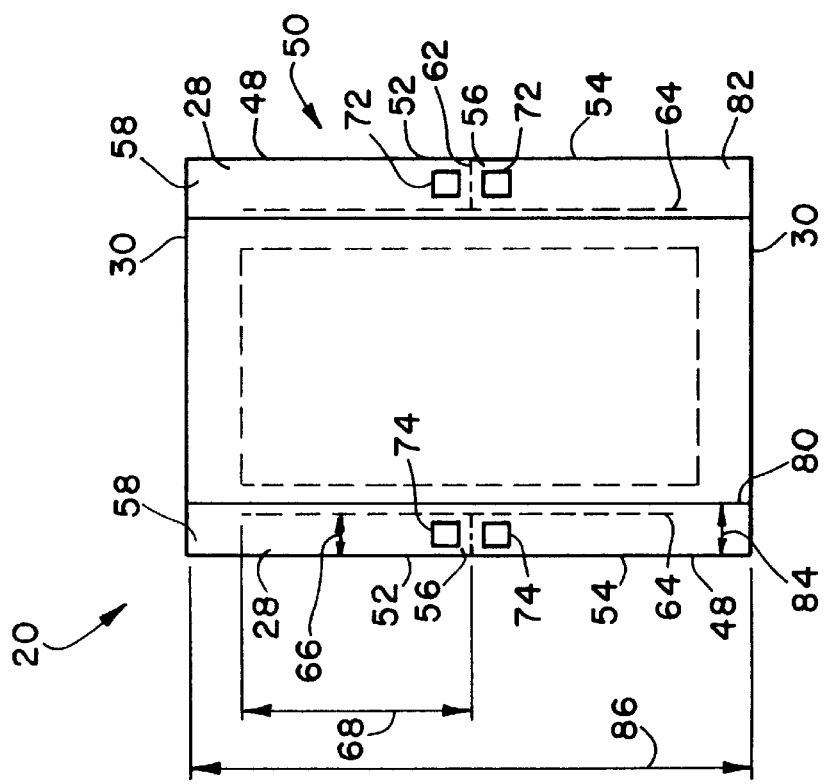

DISPOSABLE ABSORBENT ARTICLE HAVING AN INTEGRATED FASTENING SYSTEM

BACKGROUND OF THE INVENTION

The present invention relates to disposable absorbent garments such as disposable diapers and, in particular, to disposable diapers having an integrated fastening system which can be used to fasten the diaper about the waist of a wearer.

The use of fastening systems on disposable absorbent articles which are adapted to be worn about the body of a wearer such as diapers, training pants, adult incontinence products, feminine care products, and the like is well known. The fastening systems are used to fasten the article about the waist of a wearer. Conventional fastening systems typically include adhesive tape fasteners or mechanical fasteners such as hook and loop fasteners, snaps, buttons and the like which can be released and refastened a plurality of times. Generally, such fasteners can be provided directly on the absorbent article or on a separate component, such as a belt, which can be used to fasten the article about the waist of the wearer.

Conventional fastening systems for fastening disposable absorbent articles about a wearer, such as those described above, have not been completely satisfactory. For example, the conventional fastening systems which utilize fasteners attached directly to the absorbent article have required that the width dimension of the absorbent article in the front portion and back portion be sufficiently great such that the sides of the absorbent article meet or overlap along the sides of the wearer when in use. Such great widths can undesirably increase the raw material and manufacturing costs associated with producing the absorbent article. Such increased costs of some of the conventional fastening systems can result in reduced consumer acceptance.

Moreover, the conventional fastening systems which require individual belts or strips which are not integral with the absorbent article can also be costly. Such belts are expensive to manufacture and package with each individual absorbent article. Further, such non-integral belts can be inconvenient for the consumer and difficult to use.

Thus, the conventional fastening systems for disposable absorbent articles have not provided the desired level of convenience for the consumer, ease of disposability, and reduced overall cost.

SUMMARY OF THE INVENTION

In response to the discussed difficulties and problems, a new absorbent article having an integrated fastening system has been discovered.

In one aspect, the present invention concerns a disposable absorbent article which has an integrated fastening system. The disposable absorbent article includes an integrated fastening system. The integrated fastening system comprises a pair of belt segments which are integral with and provided by the end portions of the absorbent article. Each of the belt segments includes a free end which is configured to be detachable from the end portions. The integrated fastening system also comprises a fastening means for attaching the free end of each of the belt segments to the absorbent article to maintain the absorbent article about a waist of a wearer when in use.

In another aspect, the present invention concerns a disposable absorbent article which includes a front portion, a rear portion, a crotch portion connecting the front and rear portions, a pair of opposite side portions and a pair of opposite longitudinal end portions. The disposable absorbent article also comprises an outer cover, a bodyside liner, an absorbent core disposed between the bodyside liner and the outer cover and an integrated fastening system. The integrated fastening system comprises a reinforcement panel which is located on one of the end portions of the absorbent article to provide a reinforced end portion. The fastening system also comprises a belt segment which is provided by and at least partially detachable from the reinforced end portion of the absorbent article. The belt segment includes a free end which is configured to be detachable from the reinforced end portion. A fastening means is also included for attaching the free end of the belt segment to the absorbent article to maintain the absorbent article about a waist of a wearer when in use. In a particular aspect, the fastening system may also include a second belt segment which is also provided by and at least partially detachable from the reinforced end portion.

The integrated fastening system may further comprise a second reinforcement panel which is located on the opposite end portion of the absorbent article to provide a second reinforced end portion. The second reinforced end portion is configured to provide a second belt segment for use in maintaining the absorbent article about the waist of the wearer.

In yet another aspect, the present invention concerns a disposable absorbent article which includes a front portion, a rear portion, a crotch portion connecting the front and rear portions, a pair of opposite side portions and a pair of opposite longitudinal end portions. The disposable absorbent article comprises an outer cover, a bodyside liner, an absorbent core disposed between the bodyside liner and the outer cover and an integrated fastening system. The integrated fastening system comprises a reinforcement panel which is located on at least one of the side portions of the absorbent article to provide a reinforced side portion and a belt segment which is provided by and at least partially detachable from the reinforced side portion. The belt segment includes a free end which is configured to be detachable from the reinforced side portion. The fastening system also includes a fastening means for attaching the free end of the belt segment to the absorbent article to maintain the absorbent article about a waist of a wearer when in use. In a particular aspect, the integrated fastening system further comprises a second reinforcement panel which is located on the opposite side portion of the absorbent article to provide a second reinforced side portion which is configured to provide a second belt segment.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the claims.

FIG. 5 is a top plan view of an alternative configuration of an integrated fastening system of the disposable diaper of the present invention;

FIG. 6 is a top plan view of another alternative configuration of an integrated fastening system of the disposable diaper of the present invention;

FIG. 7 is a top plan view of another alternative configuration of an integrated fastening system of the disposable diaper of the present invention;

FIG. 8 is a top plan view of still another alternative configuration of an integrated fastening system of the disposable diaper of the present invention;

FIG. 9 is a top plan view of an alternative configuration of an integrated fastening system of the disposable diaper of the present invention; and FIG. 10 is a top plan view of another alternative configuration of an integrated fastening system of the disposable diaper of the present invention.

DETAILED DESCRIPTION OF THE INVENTION

Figure 3:
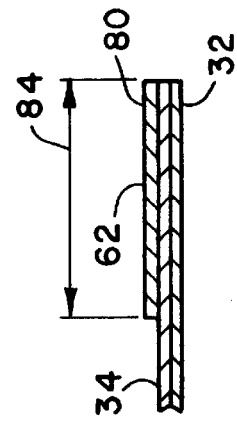
FIG. 3 is a cross-sectional view of the end portion of the disposable diaper illustrated in FIG. 2 taken along line 3—3.

The present invention relates to a disposable absorbent article having an integrated attachment system and a method of making the same. The term "disposable absorbent article" is intended to refer to any disposable article intended to be worn and attached about a wearer to absorb discharged body fluids. Examples of disposable absorbent articles include diapers, adult incontinence products, training pants, feminine care products and the like. For ease of understanding, much of the following description of the present invention will be made in terms of disposable diapers. Nonetheless, it is to be understood that the present invention is equally suited for use as any other disposable absorbent article.

As representatively illustrated in FIGS. 1–4, the diaper 20 defines a front portion 22, a rear portion 24, a crotch portion 26 connecting the front portion 22 and the rear portion 24, a pair of opposite side portions 28 and a pair of opposite longitudinal end portions 30. The diaper 20 includes a bodyside liner 32, an outer cover 34 and an absorbent core 36 located between the bodyside liner 32 and the outer cover 34. As used herein, reference to a front portion 22 refers to that part of the diaper which is generally located on the front of a wearer when in use. Reference to the rear portion 24 refers to the portion of the diaper generally located at the rear of the wearer when in use, and reference to the crotch portion 26 refers to that portion which is generally located between the legs of the wearer when in use.

The opposite side portions 28 of the diaper 20 may include a pair of elasticized, longitudinally-extending leg cuffs 38. The leg cuffs 38 are generally adapted to fit about the legs of a wearer in use and serve as a mechanical barrier to the lateral flow of body exudates. The diaper 20 may also include a front waist elastic 40 and a rear waist elastic 42. The leg cuffs 38 may be elasticized by a pair of leg elastics 44. The diaper 20 further includes an integrated fastening system 50 which is intended to hold the diaper 20 about the waist of the wearer when in use.

The bodyside liner 32 of the diaper 20, as representatively illustrated in FIGS. 1–4, suitably presents a bodyfacing surface which is compliant, soft feeling and nonirritating to the wearer's skin. Further, the bodyside liner 32 may be less hydrophilic than the absorbent core 36, to present a relatively dry surface to the wearer, and may be sufficiently porous to be liquid permeable, permitting liquid to readily penetrate through its thickness. A suitable bodyside liner 32 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 32 is suitably employed to help isolate the wearer's skin from liquids held in the absorbent core 36.

Various woven and nonwoven fabrics can be used for the bodyside liner 32. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 32 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation TRITON X-102.

The outer cover 34 of the diaper 20, as representatively illustrated in FIGS. 1–4, may suitably be composed of a material which is either liquid permeable or liquid impermeable. It is generally preferred that the outer cover 34 be formed from a material which is substantially impermeable to liquids. For example, a typical outer cover can be manufactured from a thin plastic film or other flexible liquid-impermeable material. For example, the outer cover 34 may be formed from a polyethylene film having a thickness of from about 0.012 millimeter (0.5 mil) to about 0.051 millimeter (2.0 mils). If it is desired to present the outer cover 34 with a more clothlike feeling, the outer cover 34 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 34 may be formed of a woven or nonwoven fibrous web layer which has been totally or partially constructed or treated to impart a desired level of liquid impermeability to selected regions that are adjacent or proximate the absorbent core 36. Still further, the outer cover 34 may optionally be composed of a micro-porous "breathable" material which permits vapors to escape from the absorbent core 36 while still preventing liquid exudates from passing through the outer cover 34.

The absorbent core 36 of the diaper 20, as representatively illustrated in FIGS. 1–4, may suitably comprise a matrix of hydrophilic fibers, such as a web of cellulosic fluff, mixed with particles of a high-absorbency material commonly known as superabsorbent material. In a particular embodiment, the absorbent core 36 comprises a multi-layered absorbent structure. Desirably, the absorbent core 36 comprises a top fluid acquisition layer and a bottom fluid storage layer. A suitable top fluid acquisition layer may comprise a matrix of cellulosic fluff such as wood pulp fluff. A suitable bottom fluid storage layer may include a mixture of superabsorbent hydrogel-forming particles and wood pulp fluff. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent core 36 may comprise a laminate of fibrous webs and superabsorbent material or other suitable means of maintaining a superabsorbent material in a localized area.

The absorbent core 36 may have any of a number of shapes. For example, the absorbent core may be rectangular, I-shaped or T-shaped. It is generally preferred that the absorbent core have a rectangular shape for ease of manufacturing and reduced overall cost.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core in an amount of from about 5 to about 90 weight percent based on total weight of the absorbent core 36.

The outer cover 34 and bodyside liner 32 are generally adhered to one another so as to form a pocket in which the absorbent core 36 is located. Thus, the side portions 28 and longitudinal end portions 30 of the disposable diaper 20 are suitably formed by portions of the outer cover 34, and/or bodyside liner 32, which extend beyond the sides and longitudinal ends of the absorbent core 36. The leg cuffs 38 are suitably formed from the side portions 28 but may also be formed from separate materials which are attached to the outer cover 34 and/or bodyside liner 32. Desirably, the bodyside liner 32 and outer cover 34 also have a rectangular configuration.

The leg cuffs 38, as representatively illustrated in FIGS. 1–4, may include leg elastics 44. Materials suitable for use in forming the leg elastics 44 are known to those skilled in the art. Exemplary of such materials are strands or ribbons of a polymeric, elastomeric material which are adhered to the diaper 20 at the leg cuffs 38 while in a stretched position, or which are attached to the diaper while the diaper is pleated, such that elastic constrictive forces are imparted to the leg cuffs 38. The leg cuffs 38 may be elasticized along any portion of their length which provides the desired seal against the legs of the wearer. Desirably, the leg cuffs 38 are elasticized along their entire length. Waist elastics 40 and 42, as representatively illustrated in FIGS. 1–4, are also known to those skilled in the art. The diaper 20 may also include other components, such as a pair of longitudinally extending containment flaps, as are well known. The different components of the disposable diaper 20 may be bonded together by any means known to those skilled in the art such as adhesive bonding, ultrasonic bonding, thermal bonding and the like.

Specific examples of disposable diapers on which the integrated fastening system of the present invention may be utilized are disclosed in the following U.S. patents and U.S. patent applications: U.S. Pat. No. 4,798,603 issued Jan. 17, 1989, to Meyer et al.; U.S. Pat. No. 5,135,522 issued Aug. 4, 1992, to Fahrenkrug et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. patent application Ser. No. 08/096,654 filed Jul. 22, 1993, in the name of Hanson et al.

The diaper 20 of the different aspects of the present invention also includes an integrated fastening system which is intended to be used to maintain the diaper about the waist of the wearer in use. As representatively illustrated in FIGS. 1–4, the diaper 20 includes an integrated fastening system 50 which includes a pair of integral belt segments 52 and 54. The belt segments 52 and 54 are integral with and provided by the longitudinal end portions 30 of the diaper 20. As used herein, the term "integral" refers to various portions of a single unitary element rather than separate structures which would need to be bonded to, placed with, or placed near one another. Each of the belt segments 52 and 54 includes a free end 56 which is configured to be detachable from the longitudinal end portions 30 of the diaper 20. The integrated fastening system 50 also includes a fastening means for attaching the free end 56 of each of the belt segments 52 and 54 to the diaper 20 to maintain the diaper 20 about the waist of the wearer in use.

Each belt segment 52 and 54 may be configured to be either partially or completely detachable from the longitudinal end portions 30 of the diaper 20. For example, each belt segment 52 and 54 may be completely detachable from the longitudinal end portions 30 such that each belt segment 52 and 54 provides an individual belt having two free ends 56 which can be positioned anywhere on the diaper 20 in use. However, in a particular embodiment, each belt segment 52 and 54 includes an attached end 58 which is configured to remain attached to the longitudinal end portions 30 of the diaper 20 such that the diaper 20 and the belt segments 52 and 54 remain one integral piece.

Figure 2:
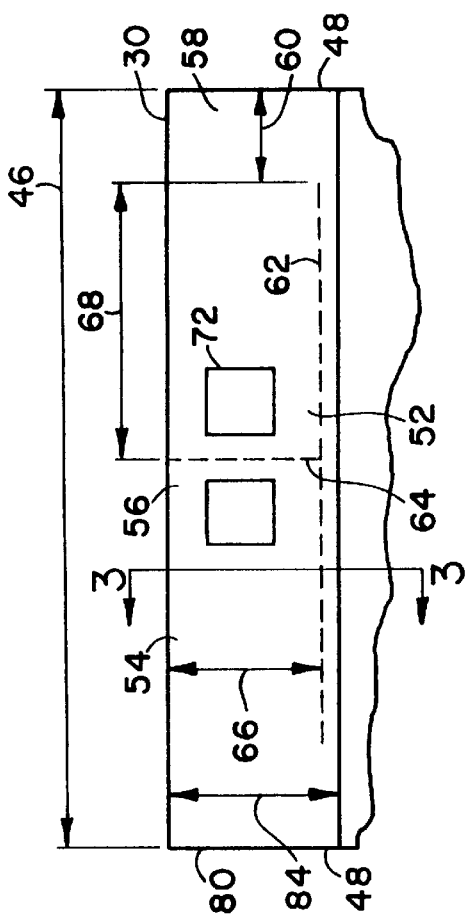
FIG. 2 is a partial top plan view of one end portion of the disposable diaper illustrated in FIG. 1.
Figure 1:
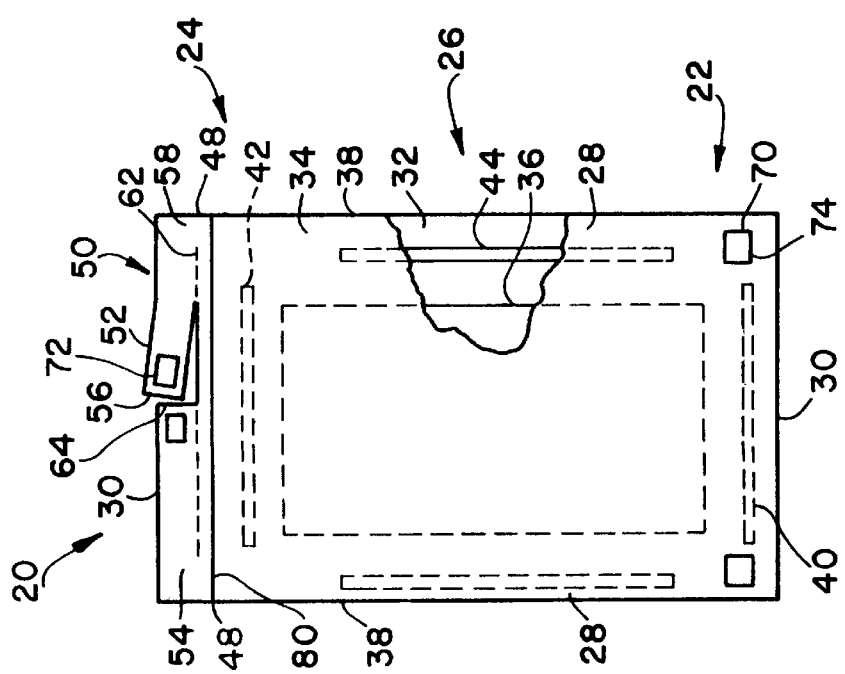
FIG. 1 is a partially cut away, top plan view of a disposable diaper of the present invention.
Figure 4:
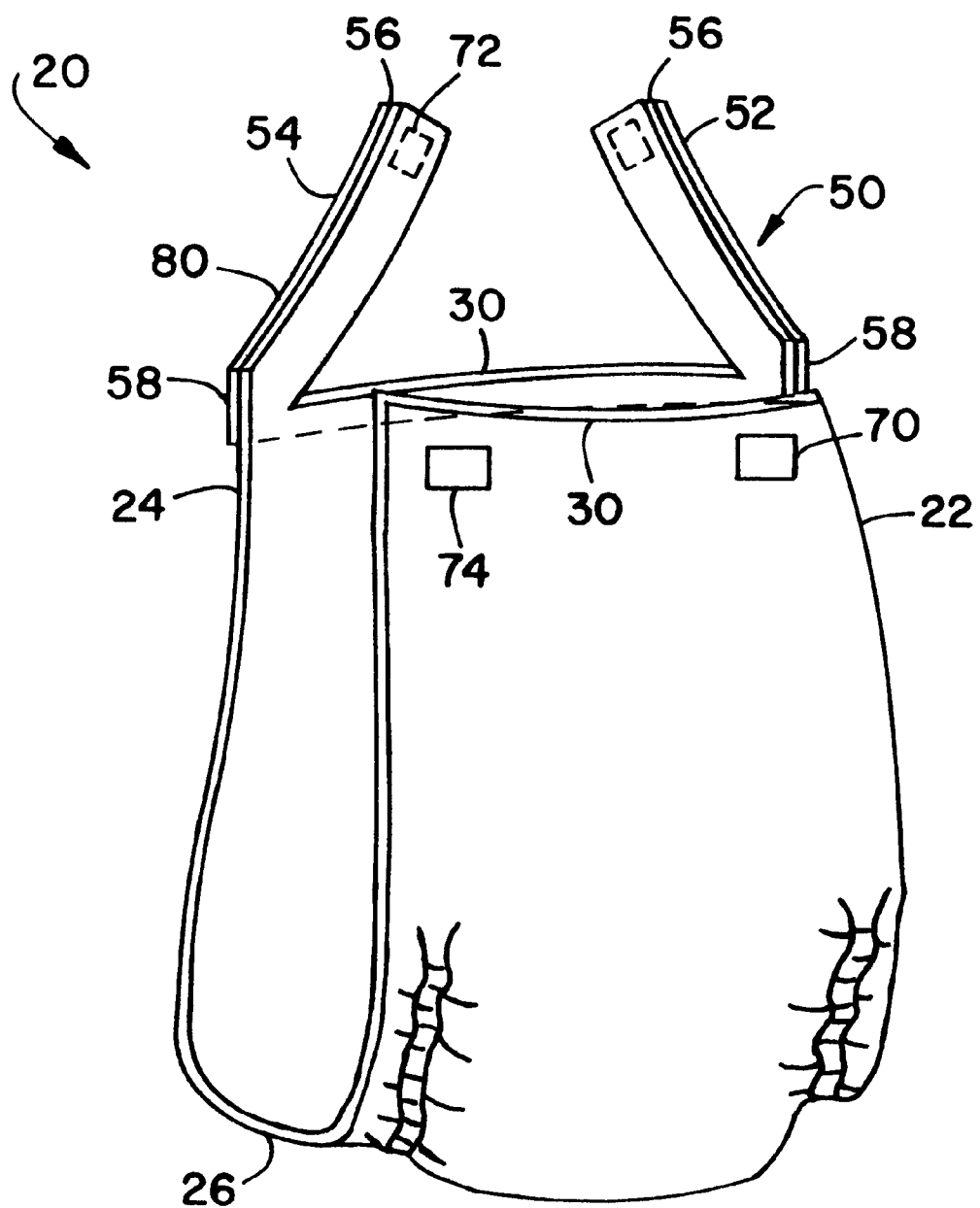
FIG. 4 is a perspective view of the disposable diaper illustrated in FIG. 1 as it is to be worn about a wearer in use.

For ease of use and disposability, it is desirable that the attached end 58 of each belt segment 52 and 54, as representatively illustrated in FIG. 2, remain attached to the longitudinal end portions 30 of the diaper 20 along an attached length 60. The attached length 60 of each belt segment 52 and 54 must be of sufficient length to provide adequate securement of the belt segment 52 and 54 to the diaper 20 when in use. For example, the attached end 58 of each belt segment 52 and 54 may have an attached length 60 of at least about 1.0 centimeters and desirably at least about 2.0 centimeters to provide an improved and reliable securement of the diaper 20 about the waist of the wearer. In a particular aspect of the invention, the attached end 58 of each belt segment 52 and 54 has an attached length 60 of from about 1.0 to about 4.0 centimeters and desirably from about 2.0 to about 3.0 centimeters.

In use, the belt segments 52 and 54 are generally wrapped around the sides of the waist of the wearer and attached to the diaper 20 to maintain the diaper about the waist of the wearer. In one embodiment of the invention as representatively illustrated in FIGS. 1–4, the belt segments 52 and 54 are provided by one longitudinal end portion 30 of the diaper 20 and have free ends 56 which are configured to be attached to the opposite longitudinal end portion 30 of the diaper 20 in use.

Thus, the belt segments 52 and 54, as representatively illustrated in FIGS. 1–4, are provided by and at least partially detachable from the longitudinal end portions 30 of the diaper 20. The longitudinal end portions 30 of the diaper 20 may suitably be formed from a wide selection of materials which may be separately attached to the diaper 20. However, in a particular embodiment, the longitudinal end portions 30 are provided by the other components of the diaper 20 such as the bodyside liner 32 or outer cover 34. For example, the bodyside liner 32 of the diaper may extend beyond the outer cover 34 and absorbent core 36 to provide the longitudinal end portions 30 of the diaper 20. Alternatively, the outer cover 34 may extend beyond the bodyside liner 32 and absorbent core 36 to provide the longitudinal end portions 30 of the diaper 20. Desirably, the longitudinal end portions 30 of the diaper 20 are provided by a composite which includes both the bodyside liner 32 and the outer cover 34 of the diaper 20 for ease of manufacturing and additional strength and reliability. As such, the belt segments 52 and 54, which are provided by the longitudinal end portions 30, may include the bodyside liner 32, the outer cover 34, a composite which includes the bodyside liner 32 and the outer cover 34 or any other suitable materials which have been attached to the diaper 20. In a particular embodiment, the longitudinal end portions 30 which provide the belt segments 52 and 54 extend beyond the longitudinal ends of the absorbent core 36 by at least about 1.5 centimeters and desirably at least about 2.5 centimeters.

The longitudinal end portions 30 and belt segments 52 and 54 may also be stretchable or elastic to allow for adjustability when fastening the diaper 20 about the waist of the wearer. As used herein, the term "stretchable" refers to a material which is capable of being elongated from about 150 to about 400 percent. The belt segments 52 and 54 may be made stretchable by any means known to those skilled in the art. For example, the material used to provide the longitudinal end portions 30 and belt segments 52 and 54 may be inherently stretchable. Elastic members may also be attached to the end portions 30 and belt segments 52 and 54 to render them stretchable. Exemplary of such materials are strands or ribbons of a polymeric, elastomeric material which are adhered to the longitudinal end portions 30 while in a stretched position, or which are attached to the end portions 30 while the end portions are pleated, such that elastic constrictive forces are imparted to the belt segments 52 and 54. The longitudinal end portions 30 and belt segments 52 and 54 may be elasticized along any portion of their width and length which provides the desired attachment to the wearer. Desirably, the belt segments 52 and 54 are elasticized along their entire length.

As representatively illustrated in FIGS. 2 and 3, each belt segment 52 and 54 has a belt width 66 and a belt length 68.

The belt width 66 of each belt segment 52 and 54 must be sufficient to provide reliable fastening without irritating the skin of the wearer. For example, it is desirable that each belt segment 52 and 54 has a belt width 66 of at least about 1.3 centimeters and more desirably at least about 2.5 centimeters to provide adequate strength and reduce the amount of red marking or irritation of the wearer.

The belt length 68 of each belt segment 52 and 54 can be varied as long as each belt segment 52 and 54 is capable of extending around the sides of the waist of the wearer and attaching to the opposite end portion of the diaper 20 to maintain the diaper 20 about the waist of the wearer. Typically, the belt length 68 of each belt segment is at least about 6.0 centimeters and desirably from about 6.0 to about 7.25 centimeters. In the aspect of the invention representatively illustrated in FIGS. 1–4, the belt length 68 is slightly less than one-half of the overall width 46 of the longitudinal end portion 30 of the diaper 20. In such a configuration, the overall width 46 of the longitudinal end portion 30 must be sufficient to provide two belt segments 52 and 54 which are capable of providing the desired securement of the diaper 20 about the waist of the wearer.

As representatively illustrated in FIGS. 1–4, the belt segments 52 and 54 are provide by one of the longitudinal end portions 30 of the diaper 20. The belt segments 52 and 54 are also configured to be at least partially detachable from the longitudinal end portions 30 of the diaper 20. In a particular embodiment, the belt segments 52 and 54 are formed by creating perforations in the longitudinal end portion 30 such that the belt segments 52 and 54 remain partially attached to the diaper 20 during manufacturing and packaging. As used herein, the term "perforations" refers to a series of cut regions and noncut regions which extend in a particular configuration. In use, the noncut regions of the line of perforations can be broken with a finger causing the belt segments 52 and 54 to become at least partially detached from the longitudinal end portion 30.

As representatively illustrated in FIGS. 1–4, one longitudinal end portion 30 of the diaper may include a lateral line of perforation 62 which extends laterally across at least a portion of the overall width 46 of the longitudinal end portion 30. In addition, a longitudinal line of perforation 64 may be created to extend longitudinally from the lateral line of perforation 62 to the longitudinal end of the diaper 20. Thus the lines of perforation 62 and 64 are configured to provide both of the belt segments 52 and 54. In the configuration illustrated in FIGS. 1–4, it is desirable that the lateral line of perforation 62 not extend to the side edges 48 of the diaper 20 such that each belt segment 52 and 54 remains attached to the diaper 20. For example, the lateral line of perforation 62 may begin and end about 1.0 centimeters from the opposite side edges 48 of the diaper 20 to provide the desired attached length 60. In a particular embodiment, the longitudinal line of perforation 64 is located near the longitudinal centerline of the diaper 20 such that each belt segment 52 and 54 is approximately the same length.

The lines of perforation 62 and 64 can be provided by any means known to those skilled in the art. In a particular embodiment, the lines of perforation 62 and 64 are provided by a knife roll which has a series of raised sharp edges which are configured to provide the desired pattern of perforations on the diaper 20. The belt segments 52 and 54 may also be formed by creating lines of relative weakness in the longitudinal end portions 30 of the diaper 20 by other means such as ultrasonic or thermal deformation as are well known to those skilled in the art.

As representatively illustrated in FIGS. 1–4, the integrated fastening system 50 of the present invention also includes a fastening means 70. The fastening means 70 is configured to attach the free end 56 of each belt segment 52 and 54 to the diaper 20 to maintain the diaper 20 about the waist of the wearer. The fastening means 70 can be any means known to those skilled in the art. In the embodiment representatively illustrated in FIGS. 1–4, the fastening means 70 includes a pair of first fastening elements 72 which are attached to the free ends 56 of the belt segments 52 and 54. The fastening means 70 also includes a pair of second fastening elements 74 which are attached to the diaper 20 along the side portions 28 and near the longitudinal end portion 30 which is opposite the longitudinal end portion 30 which provides the belt segments 52 and 54. In such an arrangement, the first fastening elements 72 are configured to be releasably engageable with the second fastening elements 74. Thus, in use, each belt segment 52 and 54 is brought around the sides of the waist of the wearer and releasably engaged to the side portions 28 of the diaper 20 near the opposite longitudinal end portion 30 to maintain the diaper 20 about the waist of the wearer.

The fastening elements 72 and 74 can be any type of fasteners which are releasably engageable together as are well known to those skilled in the art. For example, the fastening elements 72 and 74 may include adhesive tape fasteners, hook and loop type fasteners, buttons, snaps and the like. In a particular embodiment, the fasteners 72 and 74 comprise complimentary hook and loop type fasteners to provide improved securement and refastenability. The fasteners 72 and 74 may be attached to the diaper 20 using methods known to those skilled in the art such as adhesive or ultrasonic bonding.

Typically, the materials which provide the side portions 28 and the longitudinal end portions 30 of the diaper 20 may not have the desired level of strength to be used as the belt segments 52 and 54. Thus, in the embodiment of the invention representatively illustrated in FIGS. 1–4, the integrated fastening system 50 may also include a reinforcement panel 80 which is located on one of the longitudinal end portions 30 of the diaper 20 to provide a reinforced end portion 30. In such a configuration, the belt segments 52 and 54 are provided by and at least partially detachable from the end portion 30 of the diaper 20 which includes the reinforcement panel 80. Thus, each belt segment 52 and 54 may be provided by a composite which includes the reinforcement panel 80 and the outer cover 34 and/or bodyside liner 32 of the diaper 20.

The reinforcement panel 80 may be sized to cover any portion of the belt segments 52 and 54 of the diaper 20 which provides the desired reinforcement to the belt segments 52 and 54. Desirably, the reinforcement panel 80 is sized such that each belt segment 52 and 54 is reinforced over substantially it's entire length and width to provide more reliable fastening. As representatively illustrated in FIGS. 1–4, it is desirable that the reinforcement panel 80 have a panel length which extends laterally across the total width 46 of the longitudinal end portion 30 of the diaper 20 to provide improved reinforcement. In addition, it is desirable that the reinforcement panel 80 has a panel width 84 which is greater than the belt width 66 of the belt segments 52 and 54. In the embodiment representatively illustrated in FIGS. 1–4, the reinforcement panel 80 has a panel width 84 of at least about 1.8 centimeters and desirably at least about 3.0 centimeters to provide improved reinforcement. When the integrated fastening system of the present invention includes a reinforcement panel 80, the perforations from the lines of perforation 62 and 64 also extend through the reinforcement panel 80.

The reinforcement panel 80 can be made from a wide variety of materials. Suitable materials include polymeric films, such as a polyethylene film, and various woven and nonwoven fabrics which may include natural or synthetic fibers. The reinforcement panel 80 may have a tensile strength of at least about 30 Newtons and desirably from about 50 to about 400 Newtons to provide the desired reinforcement of the belt segments 52 and 54. As used herein, the term "tensile strength" refers to the tensile strength value determined according to the Tensile Strength Test as set forth below. In a particular embodiment, the reinforcement panel 80 includes a nonwoven material which has a tensile strength of at least about 50 Newtons and a basis weight of about 24 grams per square meter. The reinforcement panel 80 may also be a stretchable material which is attached to the longitudinal end portion 30 of the diaper 20 in a stretched state such that the end portions 30 and belt segments 52 and 54 are also rendered stretchable.

Alternative configurations of the integrated fastening system of the diaper of the present invention are representatively illustrated in FIGS. 5–10 wherein like numerals represent like elements. In the embodiment representatively illustrated in FIG. 5, the integrated fastening system 50 includes one integral belt segment 52 and 54 on each longitudinal end portion 30 of the diaper 20. Each of the belt segments 52 and 54 has a free end 56 which is configured to be detachable from the longitudinal end portions 30. The fastening means 70 includes a pair of first fastening elements 72 which are located on the free ends 56 of the belt segments 52 and 54. A pair of second fastening elements 74 are located along the side portions 28 of the diaper 20. In such a configuration, the first fastening elements 72 are configured to be releasably engageable with the respective second fastening elements 74 which are located on the end portion 30 opposite from the end portion 30 which provides the belt segments 52 and 54. Thus, in use, each belt segment 52 and 54 is brought across the hips of the wearer and the fastening elements 72 and 74 are releasably engaged to maintain the diaper 20 about the waist of the wearer.

To provide the integral belt segments 52 and 54 representatively illustrated in FIG. 5, each longitudinal end portion 30 may include a lateral line of perforation 62 which extends laterally across at least a portion of the width of the respective end portion 30. Desirably, the lateral line of perforation 62 extends laterally across at least about 75 percent and more desirably at least about 85 percent of the width of the end portions 30. In a particular embodiment, the lateral line of perforation 62 may extend laterally from one of the side edges 48 of the diaper 20 to a position which is from about 1.0 to about 2.0 centimeters from the opposite side edge 48 of the diaper 20. Accordingly, each belt segment 52 and 54 may have a length of at least about 6.0 centimeters and desirably from about 8.0 to about 14.0 centimeters. In such an arrangement, each belt segment 52 and 54 is configured to remain attached to the diaper 20 when in use to provide ease of fastenability and disposability. It is also desirable that each belt segment 52 and 54 has a belt width 66 of at least about 1.3 centimeters and more desirably at least about 2.5 centimeters to provide adequate strength and reduce the amount of red marking or irritation of the wearer.

The embodiment of the invention representatively illustrated in FIG. 5 has the advantage that each belt segment 52 and 54 can have a length which is greater than one-half of the overall width of the longitudinal end portion 30 of the diaper 20. Thus, the overall width of the end portion 30 of the diaper 20 representatively illustrated in FIG. 5 need not be as great as the width 46 of the diaper 20 representatively illustrated in FIGS. 1–4 to provide the desired fastening about the wearer. Such a reduced width of the end portion 30 can desirably reduce the manufacturing and raw material costs for the diaper 20.

To increase the strength of each belt segment 52 and 54 in the embodiment of the invention illustrated in FIG. 5, a first reinforcement panel 80 may be located on one longitudinal end portion 30 and a second reinforcement panel 82 may be located on the opposite longitudinal end portion 30. Desirably, each reinforcement panel 80 and 82 extends across the entire width of the respective longitudinal end portion 30 such that the entire belt segment 52 and 54 is reinforced to provide the desired reliable fastening of the diaper 20 about the waist of the wearer. In such a configuration, the perforations of the lateral lines of perforation 62 also extend through the reinforcement panels 80 and 82.

FIG. 6 representatively illustrates an alternative configuration of the integrated fastening system 50 of the present invention. As representatively illustrated in FIG. 6, the integrated fastening system 50 may include a pair of integral belt segments 52 and 54 on each of the longitudinal end portions 30 of the diaper 20. Each of the belt segments 52 and 54 has a free end 56 which is configured to be detachable from the longitudinal end portions 30. The fastening means 70 includes a pair of first fastening elements 72 which are located on the free ends 56 of the pair of belt segments 52 and 54 on one longitudinal end portion 30. A pair of second fastening elements 74 are located on the free ends 56 of the pair of belt segments 52 and 54 on the opposite longitudinal end portion 30. In such a configuration, the first fastening elements 72 are configured to be releasably engageable with the respective second fastening elements 74. Thus, in use, each belt segment 52 and 54 from one longitudinal end portion 30 is brought across the hips of the wearer and fastened to the respective belt segment 52 and 54 from the opposite longitudinal end portion 30 by releasably engaging the fastening elements 72 and 74 to maintain the diaper 20 about the waist of the wearer.

To provide the pair of integral belt segments 52 and 54 representatively illustrated in FIG. 6, each longitudinal end portion 30 includes a lateral line of perforation 62 which extends laterally across at least a portion of the width of the respective end portion 30. In a particular embodiment, the lateral line of perforation 62 may extend laterally from a position about 2.0 centimeters from one of the side edges 48 of the diaper 20 to a position which is about 2.0 centimeters from the opposite side edge 48 of the diaper 20. Each longitudinal end portion 30 also includes a longitudinal line of perforation 64 which extends longitudinally from the respective lateral line of perforation 62 to a longitudinal end of the diaper 20 to provide one pair of belt segments 52 and 54. In such a configuration, each longitudinal end portion 30 of the diaper is configured to provide a pair of belt segments 52 and 54 which remain attached to the diaper 20 when in use. It is desirable that each belt segment 52 and 54 have a length of at least about 6.0 centimeters and desirably from about 6.0 to about 8.0 centimeters. It is also desirable that each belt segment 52 and 54 has a belt width 66 of at least about 1.3 centimeters and more desirably at least about 2.5 centimeters to provide adequate strength and reduce the amount of red marking or irritation of the wearer.

The embodiment of the invention representatively illustrated in FIG. 6 has the advantage that two belt segments are used on each side of the diaper 20 to fasten the diaper about the waist of the wearer. Thus, the overall width of the end portion 30 of the diaper 20 representatively illustrated in FIG. 6 need not be as great as the width 46 of the diaper 20 representatively illustrated in FIGS. 1–4 to provide the desired fastening about the wearer.

To increase the strength of each pair of belt segments 52 and 54 in the embodiment of the invention illustrated in FIG. 6, a first reinforcement panel 80 may be located on one longitudinal end portion 30 and a second reinforcement panel 82 may be located on the opposite longitudinal end portion 30. Desirably, each reinforcement panel 80 and 82 extends across the entire width of the respective longitudinal end portion 30 such that the each pair of belt segments 52 and 54 is entirely reinforced to provide the desired reliable fastening about the waist of the wearer. In such a configuration, the perforations of the lines of perforation 62 and 64 also extend through the reinforcement panels 80 and 82.

FIG. 7 representatively illustrates an alternative configuration of the integrated fastening system 50 of the present invention. As representatively illustrated in FIG. 7, the integrated fastening system 50 includes a pair of integral belt segments 52 and 54 which are provided by and at least partially detachable from one longitudinal end portion 30 of the diaper 20. Each of the belt segments 52 and 54 has a free end 56 which is configured to be detachable from the longitudinal end portion 30. The fastening means 70 includes a pair of first fastening elements 72 which are located on the free ends 56 of the belt segments 52 and 54. A pair of second fastening elements 74 are located on the side portions 28 of the diaper 20 near the opposite longitudinal end portion 30. In such a configuration, the first fastening elements 72 are configured to be releasably engageable with the respective second fastening elements 74. Thus, in use, each belt segment 52 and 54 is brought across the hips of the wearer and fastened to the respective side portion 28 of the diaper 20 near the opposite longitudinal end portion 30 by releasably engaging the fastening elements 72 and 74 to maintain the diaper 20 about the waist of the wearer.

To provide the integral belt segments 52 and 54 representatively illustrated in FIG. 7, the one longitudinal end portion 30 may include two lateral lines of perforation 62 which extend laterally across at least a portion of the width of the end portion 30. In a particular embodiment, a first lateral line of perforation 62 may extend laterally from one side edge 48 of the diaper 20 to a position which is about 2.0 centimeters from the opposite side edge 48 of the diaper 20 to provide the first belt segment 52. A longitudinal line of perforation 64 may extend longitudinally from the first lateral line of perforation 62 to a second lateral line of perforation 62 which extends between the side portions 28 of the diaper 20 to provide the second belt segment 54. In such a configuration, one longitudinal end portion 30 of the diaper 20 is configured to provide the pair of belt segments 52 and 54 which remain attached to the diaper 20 when in use. It is desirable that each belt segment 52 and 54 have a length of at least about 6.0 centimeters and desirably from about 8.0 to about 14.0 centimeters. It is also desirable that each belt segment 52 and 54 has a belt width 66 of at least about 1.3 centimeters and more desirably at least about 2.5 centimeters to provide adequate strength and reduce the amount of red marking or irritation of the wearer.

The embodiment of the invention representatively illustrated in FIG. 7 has the advantage that both belt segments 52 and 54 are provided by the same longitudinal end portion 30 to provide improved manufacturability and ease of fastening. In addition, the length of each belt segment 52 and 54 can be greater than one-half the overall width of the end portion 30 of the diaper 20. Thus, the overall width of the end portion 30 of the diaper 20 representatively illustrated in FIG. 7 need not be as great as the width 46 of the diaper 20 representatively illustrated in FIGS. 1–4 to provide the desired fastening about the wearer.

To increase the strength of the belt segments 52 and 54 in the embodiment of the invention representatively illustrated in FIG. 7, a reinforcement panel 80 may be located on the longitudinal end portion 30 of the diaper 20 which provides the belt segments 52 and 54. Desirably, the reinforcement panel 80 extends across the entire width of the longitudinal end portion 30 such that the each of the belt segments 52 and 54 is entirely reinforced to provide the desired reliable fastening about the waist of the wearer. The reinforcement panel 80 may also have a panel width 84 which at least wide enough to reinforce both belt segments 52 and 54. Desirably, each belt segment 52 and 54 has a belt width of at least about 1.3 centimeters and the reinforcement panel 80 has a panel width of at least about 1.8 centimeters. In such a configuration, the perforations of the lines of perforation 62 and 64 also extend through the reinforcement panel 80.

FIG. 8 representatively illustrates another alternative configuration of the integrated fastening system 50 of the present invention. As representatively illustrated in FIG. 8, the integrated fastening system 50 includes a pair of integral belt segments 52 and 54 which are provided by and at least partially detachable from one longitudinal end portion 30 of the diaper 20. Each of the belt segments 52 and 54 has a free end 56 which is configured to be detachable from the longitudinal end portion 30. The fastening means 70 includes a pair of first fastening elements 72 which are located on the free ends 56 of the belt segments 52 and 54. A pair of second fastening elements 74 are located on the side portions 28 of the diaper 20 near the opposite longitudinal end portion 30. In such a configuration, the first fastening elements 72 are configured to be releasably engageable with the respective second fastening elements 74. Thus, in use, each belt segment 52 and 54 is brought across the hips of the wearer and fastened to the respective side portion 28 of the diaper 20 near the opposite longitudinal end portion 30 by releasably engaging the fastening elements 72 and 74.

The integral belt segments 52 and 54 representatively illustrated in FIG. 8, are provided in a similar manner to the belt segments illustrated in FIGS. 1–4, except that each belt segment 52 and 54 includes two additional lines of perforation 62 and 64 which selectively divide each belt segment 52 and 54 such that they are extendable an additional distance when in use. In such a configuration, one longitudinal end portion 30 of the diaper 20 is configured to provide a pair of belt segments 52 and 54 which remain attached to the diaper 20 when in use. It is desirable that each belt segment 52 and 54 have a length of at least about 6.0 centimeters and desirably from about 8.0 to about 14.0 centimeters. It is also desirable that each belt segment 52 and 54 has a belt width 66 of at least about 1.3 centimeters and more desirably at least about 2.5 centimeters to provide adequate strength and reduce the amount of red marking or irritation of the wearer.

The embodiment of the invention representatively illustrated in FIG. 8 has the advantage that both belt segments 52 and 54 are provided by the same longitudinal end portion 30 to provide improved manufacturability and ease of fastening. In addition, the extendable length of each belt segment 52 and 54 can be greater than one-half the overall width of the end portion 30 of the diaper 20. Thus, the overall width of the end portion 30 of the diaper 20 representatively illustrated in FIG. 8 need not be as great as the width 46 of the diaper 20 representatively illustrated in FIGS. 1–4 to provide the desired fastening about the wearer.

To increase the strength of the belt segments 52 and 54 in the embodiment of the invention representatively illustrated in FIG. 8, a reinforcement panel 80 may be located on the longitudinal end portion 30 of the diaper 20 which provides the belt segments 52 and 54. Desirably, the reinforcement panel 80 extends across the entire width of the longitudinal end portion 30 such that the each of the belt segments 52 and 54 is entirely reinforced to provide the desired reliable fastening about the waist of the wearer. In such a configuration, the perforations of the lines of perforation 62 and 64 also extend through the reinforcement panel 80.

FIG. 9 representatively illustrates an alternative configuration of the integrated fastening system 50 of the present invention wherein the belt segments 52 and 54 are provided by and at least partially detachable from the side portions 28 of the diaper 20. As representatively illustrated in FIG. 9, each side portion 28 of the diaper 20 provides a pair of belt segments 52 and 54 which have free ends 56 which are configured to be detachable from the side portion 28. The fastening means 70 includes a pair of first fastening elements 72 which are located on the free ends 56 of the belt segments 52 and 54 located on one side portion 28 of the diaper 20. A pair of second fastening elements 74 are located on the belt segments 52 and 54 on the opposite side portion 28 of the diaper 20. In such a configuration, the first fastening elements 72 are configured to be releasably engageable with the respective second fastening elements 74. Thus, in use, each pair of belt segments 52 and 54 from one side portion 28 is brought across the hips of the wearer and fastened to the respective belt segments 52 and 54 from the opposite side portion 28 of the diaper 20 by releasably engaging the fastening elements 72 and 74.

The integral belt segments 52 and 54 representatively illustrated in FIG. 9 may be provided by any manner known to those skilled in the art. For example, each side portion 28 of the diaper 20 may include a longitudinal line of perforation 64 which extends longitudinally along at least a portion of the length of the side portion 28. A lateral line of perforation 62 may then extend laterally from the longitudinal line of perforation 64 to the side edge 48 of the diaper 20. In such a configuration, each side portion 28 of the diaper 20 is configured to provide a pair of belt segments 52 and 54 which remain attached to the diaper 20 when in use. It is desirable that each belt segment 52 and 54 have a length of at least about 6.0 centimeters and desirably from about 8.0 to about 14.0 centimeters. It is also desirable that each belt segment 52 and 54 has a belt width 66 of at least about 1.3 centimeters and more desirably at least about 2.5 centimeters to provide adequate strength and reduce the amount of red marking or irritation of the wearer.

To increase the strength of the belt segments 52 and 54 in the embodiment of the invention representatively illustrated in FIG. 9, a pair of reinforcement panels 80 and 82 are located on the side portions 28 of the diaper 20. Desirably, the reinforcement panels 80 and 82 extend longitudinally along the entire length of the side portion 28 such that each of the belt segments 52 and 54 is entirely reinforced to provide the desired reliable fastening about the waist of the wearer. In such a configuration, the perforations of the lines of perforation 62 and 64 also extend through the reinforcement panels 80 and 84.

FIG. 10 representatively illustrates another alternative configuration of the integrated fastening system 50 of the present invention wherein the belt segments 52 and 54 are provided by and at least partially detachable from the side portions 28 of the diaper 20. As representatively illustrated in FIG. 10, each side portion 28 of the diaper 20 provides a belt segment 52 and 54 which has a free end 56 which is configured to be detachable from the side portion 28. The fastening means 70 includes a pair of first fastening elements 72 which are located on the free ends 56 of the belt segments 52 and 54. A pair of second fastening elements 74 which are configured to be releasably engageable with the first fastening elements 72 are located on the diaper 20. Thus, in use, each belt segment 52 and 54 is brought across the hips of the wearer and fastened to the diaper 20 by releasably engaging the fastening elements 72 and 74 to maintain the diaper 20 about the waist of the wearer.

The integral belt segments 52 and 54 representatively illustrated in FIG. 10 may be provided by any manner known to those skilled in the art. For example, each side portion 28 of the diaper 20 may include a longitudinal line of perforation 64 which extends longitudinally along at least a portion of the length of the side portion 28. Desirably, the line of perforation 64 extends longitudinally along at least about 80 percent of the length of the side portions 28. The belt length 68 of each belt segment 52 and 54 can be any length which provides the desired fastenability. For example, each longitudinal line of perforation 64 may extend from one longitudinal end of the diaper 20 to a position about 2.0 centimeters from the opposite longitudinal end of the diaper 20. Such a belt segment desirably has a belt length 68 of at least about 20 centimeters and more desirably at least about 30 centimeters to easily accommodate different wearer sizes and allow the overall width of the diaper 20 to be relatively small. In such a configuration, each side portion 28 of the diaper 20 is configured to provide a belt segments 52 and 54 which remains attached to the diaper 20 when in use for ease of disposability and fastening. It is also desirable that each belt segment 52 and 54 has a belt width 66 of at least about 1.3 centimeters and more desirably at least about 2.5 centimeters to provide adequate strength and reduce the amount of red marking or irritation of the wearer.

To increase the strength of the belt segments 52 and 54 in the embodiment of the invention representatively illustrated in FIG. 10, a pair of reinforcement panels 80 and 82 are located on the side portions 28 of the diaper 20. Desirably, the reinforcement panels 80 and 82 have a panel length 86 which extends longitudinally along the entire length of the side portion 28 such that each of the belt segments 52 and 54 is entirely reinforced to provide the desired reliable fastening about the waist of the wearer. In such a configuration, the perforations of the lines of perforation 64 also extend through the reinforcement panels 80 and 84. The reinforcement panels 80 and 82 may also have a panel width 84 which is at least as great as the belt width 66 of each belt segment.

The different aspects of the present invention, as representatively illustrated in FIGS. 1–10, provide a disposable absorbent article which has an integrated fastening system. The integrated fastening system includes belt segments which are integral with the absorbent article to provide ease of manufacturing and fastening about the wearer. In such a configuration, an extraneous fastening belt is not required thus reducing the manufacturing and raw material costs. In a particular embodiment of the present invention, the integral belt segments are reinforced along their entire length and width to provide a stronger and more reliable fastening about the waist of the wearer.

TENSILE STRENGTH TEST

This test procedure determines the peak tensile load, measured in pounds-force, of a material when only a portion of the sample material width is centrally gripped by the testing equipment.

EQUIPMENT

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 5213 Tensile Tester with Sintech QAD (Quality Assurance Department) Software.
2. QAD software commercially obtained from MTS Sintech under the trade designation QAD Software.
3. 1 inch×3 inch lower jaw facing commercially available from Instron Corporation, Canton, Mass.
4. 1 inch×1 inch upper jaw facing commercially available from Instron Corporation, Canton, Mass.

TEST PROCEDURE

1. The load cell is calibrated and the QAD software loaded.
2. The jaws are installed on the tensile tester.
3. The test condition for the tensile tester are set as follows:
   Crosshead speed: 300 millimeters/minute
   Full-scale load: 50 kilograms
   Threshold: 3 percent
   Fail criterion: 40 percent
   Gage length: 3 inches
4. The weight of the jaws is tared out.
5. The material is cut to provide a sample having a width of 4.0 inches and a length of 6.0 inches.
6. The material is symmetrically inserted into the jaws with the length being parallel to the direction of the load application.
7. The crosshead is started in motion.
8. The peak load of failure is recorded.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A disposable absorbent article which includes an absorbent core having a pair of longitudinally opposed end edges and a pair of laterally opposed side edges, a front portion, a rear portion, a crotch portion connecting said front and rear portions, a pair of opposite side portions and a pair of opposite longitudinal end portions which extend longitudinally beyond said end edges and laterally between said side edges of said absorbent core, said disposable absorbent article comprising an integrated fastening system which comprises:

a) a pair of belt segments which are integral with and at least partially provided by said end portions of said absorbent article wherein each of said belt segments includes a free end which is configured to be detachable from said end portions; and b) a fastening means for attaching said free end of each of said belt segments to said absorbent article to maintain said absorbent article about a waist of a wearer when in use.

2. The disposable absorbent article according to claim 1 wherein said absorbent article further comprises a pair of elasticized longitudinally extending leg cuffs which are located along said pair of opposite side portions of said absorbent article.

3. The disposable absorbent article according to claim 1 wherein said absorbent article includes an outer cover and said belt segments are provided by said outer cover of said absorbent article.

4. The disposable absorbent article according to claim 1 wherein said absorbent article includes a bodyside liner and said belt segments are provided by said bodyside liner of said absorbent article.

5. The disposable absorbent article according to claim 1 wherein said absorbent article includes an outer cover and a bodyside liner and said belt segments are provided by a composite which includes said outer cover and said bodyside liner of said absorbent article.

6. The disposable absorbent article according to claim 1 wherein said belt segments are stretchable.

7. The disposable absorbent article according to claim 6 wherein said belt segments include a plurality of elastic strands.

8. The disposable absorbent article according to claim 1 wherein each of said belt segments has a belt width of at least 1.3 centimeters.

9. The disposable absorbent article according to claim 1 wherein one of said end portions of said absorbent article includes a lateral line of perforation which extends laterally across at least a portion of a width of said one end portion to provide at least one of said belt segments.

10. The disposable absorbent article according to claim 9 wherein said one end portion of said absorbent article further includes a longitudinal line of perforation which extends longitudinally from said lateral line of perforation to a longitudinal end of said absorbent article to provide both of said belt segments.

11. The disposable absorbent article according to claim 1 wherein each of said end portions of said absorbent article includes a lateral line of perforation which extends laterally across at least a portion of a width of said end portion and wherein each of said end portions provides one of said belt segments.

12. The disposable absorbent article according to claim 11 wherein said lateral lines of perforation extend laterally across at least 75 percent of said width of said end portions.

13. The disposable absorbent article according to claim 1 wherein each of said belt segments includes an attached end which is configured to remain attached to said end portions of said absorbent article.

14. The disposable absorbent article according to claim 13 wherein said attached end of each of said belt segments is configured to remain attached to said end portions of said absorbent article along an attached length of at least 1.0 centimeter.

15. The disposable absorbent article according to claim 1 wherein said fastening means includes a first fastening element located on said free end of each of said belt segments and a second fastening element located on said absorbent article, wherein said first fastening elements are configured to be releasably engageable with said second fastening elements to maintain said absorbent article about said wearer when in use.

16. The disposable absorbent article according to claim 15 wherein said first and second fastening elements include adhesive tape fasteners.

17. The disposable absorbent article according to claim 15 wherein said first and second fastening elements include hook and loop type fasteners.

18. A disposable absorbent article which includes an absorbent core having a pair of longitudinally opposed end edges and a pair of laterally opposed side edges, a front portion, a rear portion, a crotch portion connecting said front and rear portions, a pair of opposite side portions and a pair of opposite longitudinal end portions which extend longitudinally beyond said end edges and laterally between said side edges of said absorbent core, said disposable absorbent article comprising:

a) an outer cover;
b) a bodyside liner;
c) said absorbent core being disposed between said bodyside liner and said outer cover; and
d) an integrated fastening system, said integrated fastening system comprising:
   i) a reinforcement panel which is located on one of said end portions of said absorbent article to provide a reinforced end portion;
   ii) a belt segment which is at least partially provided by and at least partially detachable from said reinforced end portion of said absorbent article wherein substantially an entire length and width of said belt segment is reinforced by said reinforcement panel and wherein said belt segment includes a free end which is configured to be detachable from said reinforced end portion; and
   iii) a fastening means for attaching said free end of said belt segment to said absorbent article to maintain said absorbent article about a waist of a wearer when in use.

19. The disposable absorbent article according to claim 18 wherein said reinforcement panel is attached to said outer cover of said absorbent article to provide said reinforced end portion.

20. The disposable absorbent article according to claim 18 wherein said reinforcement panel is attached to said bodyside liner of said absorbent article to provide said reinforced end portion.

21. The disposable absorbent article according to claim 18 wherein said belt segment is provided by a composite which includes said outer cover and said reinforcement panel.

22. The disposable absorbent article according to claim 18 wherein said belt segment is provided by a composite which includes said bodyside liner and said reinforcement panel.

23. The disposable absorbent article according to claim 18 wherein said belt segment is provided by a composite which includes said outer cover, said bodyside liner and said reinforcement layer.

24. The disposable absorbent article according to claim 18 wherein said belt segment is stretchable.

25. The disposable absorbent article according to claim 18 wherein said belt segment has a belt width of at least 1.3 centimeters.

26. The disposable absorbent article according to claim 18 wherein said belt segment includes an attached end which is configured to remain attached to said reinforced end portion of said absorbent article.

27. The disposable absorbent article according to claim 26 wherein said attached end of said belt segment is configured to remain attached to said reinforced end portion of said absorbent article along an attached length of at least 2.0 centimeters.

28. The disposable absorbent article according to claim 18 wherein said reinforced end portion includes a lateral line of perforation which extends laterally across at least a portion of a width of said reinforced end portion to provide said belt segment.

29. The disposable absorbent article according to claim 28 wherein said reinforced end portion of said absorbent article further includes a longitudinal line of perforation which extends longitudinally from said lateral line of perforation to a longitudinal end of said absorbent article to provide a pair of said belt segments.

30. The disposable absorbent article according to claim 18 wherein said integrated fastening system further comprises a second reinforcement panel which is located on said opposite end portion of said absorbent article to provide a second reinforced end portion which is configured to provide a second belt segment.

31. The disposable absorbent article according to claim 30 wherein said second reinforced end portion includes a lateral line of perforation which extends laterally across at least a portion of a width of said second reinforced end portion to provide said second belt segment.

32. The disposable absorbent article according to claim 18 wherein said fastening means includes a first fastening element which is located on said free end of said belt segment and a second fastening element located on said absorbent article, wherein said first fastening element is configured to be releasably engageable with said second fastening element to maintain said absorbent article about said wearer when in use.

33. The disposable absorbent article according to claim 18 wherein said reinforcing panel is a nonwoven material.

34. The disposable absorbent article according to claim 18 wherein said reinforcing panel is a polyethylene material.

* * * * *